United States Patent
Heeney et al.

(10) Patent No.: US 6,841,677 B2
(45) Date of Patent: Jan. 11, 2005

(54) MONO-, OLIGO- AND POLYDITHIENOPYRIDINE

(75) Inventors: Martin Heeney, Southampton (GB); Steven Tierney, Southampton (GB); Marcus Thompson, Fordingbridge Hampshire (GB); Mark Giles, Southampton (GB); Louise Farrand, Dorset (GB); Maxim Shkunov, Southampton (GB); David Sparrowe, Dorset (GB); Iain McCulloch, Kings Somborne (GB)

(73) Assignee: Merck Patent Gesellschaft Mit Beschraenkter, Darmstadt (DE)

( * ) Notice: Subject to any disclaimer, the term of this patent is extended or adjusted under 35 U.S.C. 154(b) by 67 days.

(21) Appl. No.: 10/190,622

(22) Filed: Jul. 9, 2002

(65) Prior Publication Data

US 2003/0047719 A1 Mar. 13, 2003

(30) Foreign Application Priority Data

Jul. 9, 2001 (EP) .............................. 01115743

(51) Int. Cl.$^7$ ..................... H01B 1/12; C08F 126/06; C08F 128/06; C07D 505/00; C09K 19/34
(52) U.S. Cl. ................... 546/80; 526/288; 252/500; 252/299.61
(58) Field of Search .................. 252/500, 299.01, 252/299.2, 299.61; 526/256, 259–288; 546/80

(56) References Cited

U.S. PATENT DOCUMENTS 5,380,807 A * 1/1995 Havinga et al. ............ 526/257
6,645,401 B2 * 11/2003 Giles et al. ................. 252/500

OTHER PUBLICATIONS

"Synthesis and reactivity of alkyl (4–aminothien–3–yl)carbamates" ☐☐Delphine Brugier et al, Tetrahedron, vol. 53, Issue 30 , Jul. 28, 1997, pp. 10331–10344. Abstract.*

"Synthesis of dithienol[3,2–b:2',3'–e]pyridines and 4,8–dihydrodithieno[3'2–b:2'–e]pyridines", Outurquin, Francis, Tetrahedron Letters (1993), 34(36), 5719–22. Abstract.*

* cited by examiner

*Primary Examiner*—Mark Kopec
(74) *Attorney, Agent, or Firm*—Millen White Zelano & Branigan P.C.

(57) ABSTRACT

The invention relates to new conjugated mono-, oligo- and polydithienopyridines, their use as semiconductors or charge transport materials in optical, electrooptical or electronic devices including field effect transistors, electroluminescent, photovoltaics, sensors and electrophotographic recording devices, and to a field effect transistor as a component of integrated circuitry, as a thin fim transistor in flat panel display applications or for RFID tags, or a semiconducting component in organic light-emitting diode applications, comprising the new mono-, oligo and polydithienopyridines.

28 Claims, No Drawings

MONO-, OLIGO- AND POLYDITHIENOPYRIDINE

FIELD OF INVENTION

The invention generally relates to 125 new conjugated mono-, oligo- and polydithienopyridines. The invention may further relate to their use as semiconductors or charge transport materials in optical, electrooptical or electronic devices including field effect transistors, electroluminescent, photovoltaic and sensor devices. The invention can further relate to field effect transistors and semiconducting components comprising the new mono-, oligo and polydithienopyridines.

BACKGROUND AND PRIOR ART

Organic materials have recently shown promise as the active layer in organic based thin film transistors and organic field effect transistors [see reference 1]. Such devices have potential applications in smart cards, security tags and the switching element in flat panel displays. Organic materials are envisaged to have substantial cost advantages over their silicon analogues if they can be deposited from solution, as this enables a fast, large-area fabrication route.

The performance of the device is principally based upon the charge carrier mobility of the semiconducting material and the current on/off ratio, so the ideal semiconductor should have a low conductivity in the off state, combined with a high charge carrier mobility ($>1\times10^{-3}$ cm$^2$V$^{-1}$ s$^{-1}$). In addition, it is important that the semiconducting material is relatively stable to oxidation i.e. it has a high ionisation potential, as oxidation leads to reduced device performance.

A known compound which has been shown to be an effective p-type semiconductor for organic FETs is bis (dithienothiophene) (BDT) [see reference 2–4]. When deposited as a thin film by vacuum deposition, it was shown to have carrier mobilities between $1\times10^{-3}$ and $5\times10^{-2}$ cm$^2$V$^{-1}$ s$^{-1}$ and very high current on/off ratios (up to $10^8$). However, vacuum deposition is an expensive processing technique that is unsuitable for the fabrication of large-area films.

Regioregular poly(3-hexylthiophene) has been reported with charge carrier mobility between $1\times10^{-5}$ and $4.5\times10^{-2}$ cm$^2$V$^{-1}$ s$^{-1}$, but with a rather low current on/off ratio ($10-10^3$) [see reference 5]. In general, poly(3-alkylthiophenes) show improved solubility and are able to be solution processed to fabricate large area films. However, poly(3-alkylthiophenes) have relatively low ionisation potentials and are susceptible to doping in air [see reference 6].

It is the aim of the present invention to provide new materials for use as semiconductors or charge transport materials, which are easy to synthesize, have high charge mobility, good processibility and improved oxidative stability. Other aims of the invention are immediately evident to those skilled in the art from the following description.

SUMMARY OF THE INVENTION

The inventors have found that these aims can be achieved by providing new oligomers and polymers based on dithienopyridine. Dithieno[3,2-b:2'3'-e]pyridine (DTP) of formula (2) below, which is the pyridine analogue of dithienothiophene (DTT) (1) of formula 1 below, is a more π-electron deficient heterocycle than DTT due to the high electronegativity of nitrogen. As a result, dithieno[3,2-b:2'3'-e]pyridine has a lower HOMO (Highest Occupied Molecular Orbital) than DTT, and therefore a higher oxidation potential making it more stable to oxidation.

DTT 1

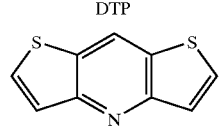

DTP 2

Also, whilst the synthesis of DTT contains many low yielding steps [see reference 7], DTP can be synthesized more easily via the acid catalysed reaction of 3-thiophenamine with an aldehyde [see reference 8]. Using this procedure, various substituents including alkyl, alkenyl, aryl and heteroaryl groups can be selectively and easily introduced through modification of the aldehyde employed.

A further aspect of the invention relates to reactive mesogens consisting of a central core comprising one or more DTP units, and optionally comprising further unsaturated organic groups that form a conjugated system together with the DTP units, said core being linked, optionally via a spacer group, to one or two polymerisable groups. The reactive mesogens can induce or enhance liquid crystal phases or are liquid crystalline themselves. They can be oriented in their mesophase and the polymerisable group can be polymerised or crosslinked in situ to form polymer films with a high degree of order, thus yielding improved semiconductor materials with high stability and high charge carrier mobility.

A further aspect of the invention relates to liquid crystal polymers, in particular liquid crystal side chain polymers, obtained from the reactive mesogens comprising one or more DTP units, which are then further processed e.g. from solution as thin layers for use in semiconductor devices.

The terms 'liquid crystalline or mesogenic material' or 'liquid crystalline or mesogenic compound' means materials or compounds comprising one or more rod-shaped, lath-shaped or disk-shaped mesogenic groups, i.e. groups with the ability to induce liquid crystal phase behaviour. The compounds or materials comprising mesogenic groups do not necessarily have to exhibit a liquid crystal phase themselves. It is also possible that they show liquid crystal phase behaviour only in mixtures with other compounds, or when the mesogenic compounds or materials, or the mixtures thereof, are polymerised.

The term 'polymerisable' includes compounds or groups that are capable of participating in a polymerisation reaction, like radicalic or ionic chain polymerisation, polyaddition or polycondensation, and reactive compounds or reactive groups that are capable of being grafted for example by condensation or addition to a polymer backbone in a polymeranaloguous reaction.

The term 'film' includes self-supporting, i.e. free-standing, films that show more or less pronounced mechanical stability and flexibility, as well as coatings or layers on a supporting substrate or between two substrates.

One feature of the invention are mono-, oligo- and polymers comprising at least one dithienopyridine group.

A further feature of the present invention is novel intermediates and process steps described hereinafter.

Another feature of the invention is the use of mono-, oligo- and polydithienopyridines according to the invention as semiconductors or charge transport materials, in particular in optical, electrooptical or electronic devices, like for example in field effect transistors (FET) as components of integrated circuitry, as thin film transistors in flat panel display applications or for Radio Frequency Identification (RFID) tags, or in semiconducting components for organic light emitting diode (OLED) applications such as electroluminescent displays or backlights of e.g. liquid crystal displays, for photovoltaic or sensor devices, as electrode materials in batteries, as photoconductors and for electrophotographic applications like electrophotographic recording.

Another feature of the invention is a field effect transistor, for example as a component of integrated circuitry, as a thin film transistor in flat panel display applications, or in a Radio Frequency Identification (RFID) tag, comprising one or more mono-, oligo- or polydithienopyridines according to the invention.

Another feature of the invention is a semiconducting component, for example in OLED applications like electroluminescent displays or backlights of e.g. liquid crystal displays, in photovoltaic or sensor devices, as electrode materials in batteries, as photoconductors and for electrophotographic applications, comprising one or more mono-, oligo- or polydithienopyridines according to the invention.

Another feature of the invention is a security marking or device comprising an RFID or ID tag or a FET according to the invention.

The mono-, oligo- and polydithienopyridines according to the invention are especially useful as charge transport semiconductors in that they have high carrier mobilities. Particularly preferred are mono-, oligo- and polydithienopyridines wherein the dithienopyridine core is substituted by one or more alkyl or fluoroalkyl groups. The introduction of fluoroalkyl and alkyl side chains into the dithienopyridine core improves their solubility and therefore their solution processibility. Furthermore, the presence of fluoroalkyl side chains also renders them effective as n-type semiconductors. The electron-withdrawing nature of the fluoroalkyl substituents will also lower the HOMO further and result in a more stable material, which is less susceptible to oxidation.

Particularly preferred are mono-, oligo- and polymers comprising at least one dithienopyridine group and at least one reactive group that is capable of a polymerisation or crosslinking reaction.

Further preferred are mono-, oligo- and polymers comprising at least one dithienopyridine group that are mesogenic or liquid crystalline.

Further preferred are oligo- and polymers comprising at least two recurring units, at least one of which comprises one or more dithienopyridine groups.

Particularly preferred are mono-, oligo- and polymers comprising one or more identical or different recurring units of formula I

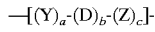

wherein

D is a dithienopyridine group of formula II

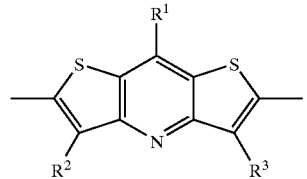

$R^1$ to $R^3$ are independently of each other H, halogen or straight chain, branched or cyclic alkyl with 1 to 20 C-atoms, which may be unsubstituted, mono- or poly-substituted by F, Cl, Br, I or CN, it being also possible for one or more non-adjacent $CH_2$ groups to be replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, $R^0$ and $R^{00}$ are independently of each other H or alkyl with 1 to 12 C-atoms, Y and Z are independently of each other —CX$^1$=CX$^2$—, —C≡C—, or optionally substituted arylene or heteroarylene, $X^1$ and $X^2$ are independently of each other H, F, Cl or CN, and a, b and c are independently of each other 0 or 1, with a+b+c>0, and wherein in at least one recurring unit b is 1.

Especially preferred are mono-, oligo- and polymers of formula I1

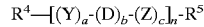

wherein Y, Z, D, a, b and c are as defined in formula I, n is an integer from 1 to 5000, $R^4$ and $R^5$ are independently of each other H, halogen, Sn(R$^0$)$_3$ or straight chain, branched or cyclic alkyl with 1 to 20 C-atoms, which may be unsubstituted, mono- or poly-substituted by F, Cl, Br, I or CN, it being also possible for one or more non-adjacent CH$_2$ groups to be replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, or denote P-Sp-X, P is a polymerisable or reactive group, Sp is a spacer group or a single bond, and X is —O—, —S—, —OCH$_2$—, —CH$_2$O—, —CO—, —COO—, —OCO—, —OCO—O—, —CO—NR$^0$—, —NR$^0$—CO—, —OCH$_2$—, —CH$_2$O—, —SCH$_2$—, —CH$_2$S—, —CH=CH—COO—, —OOC—CH=CH— or a single bond, wherein the recurring units [(Y)$_a$-(D)$_b$-(Z)$_c$] can be identical or different.

In the oligo- and polymers of the present invention the recurring units (Y)$_a$-(D)$_b$-(Z)$_c$ in case of multiple occurrence can be selected of formula I independently of each other, so that an oligo- or polymer may comprise identical or different recurring units (Y)$_a$-(D)$_b$-(Z)$_c$. The oligo- and polymers thus include homopolymers and copolymers like for example statistically random copolymers, for example with a monomer sequence such as —Y-D-Z-Z-D-Y-D-, alternating copolymers, for example with a monomer sequence such as —Y-D-Z-Y-D-Z-, and block copolymers, for example with a monomer sequence such as —Y—Y-D-D-D-Z-Z-Z-Z-, wherein the groups Y and Z form a conjugated system together with the dithienopyridine unit D.

Especially preferred are alternating copolymers.

Further preferred are mono-, oligo- and polymers comprising one or more recurring units $(Y)_a$-$(D)_b$-$(Z)_c$, wherein a=c=0 and b=1, very preferably consisting exclusively of such recurring units.

Further preferred are mono-, oligo- and polymers comprising one or more recurring units $(Y)_a$-$(D)_b$-$(Z)_c$, wherein b=c=1 and a=0, very preferably consisting exclusively of such recurring units.

Further preferred are mono-, oligo- and polymers comprising one or more recurring units $(Y)_a$-$(D)_b$-$(Z)_c$, wherein a=b=c=1, very preferably consisting exclusively of such recurring units.

Further preferred are mono-, oligo- and polymers wherein n is an integer from 2 to 5000, in particular from 100 to 1000, n is an integer from 2 to 5, n is an integer from 1 to 15 and one or both of $R^4$ and $R^5$ denote P-Sp-X, n is an integer from 2 to 5000 and $R^4$ and $R^5$ have one of the meanings of $R^1$, the molecular weight is from 30000 to 300000, $R^1$, $R^2$ and $R^3$ are selected from $C_1$–$C_{20}$-alkyl that is optionally substituted with one or more fluorine atoms, $C_1$–$C_{20}$-alkenyl, $C_1$–$C_{20}$-alkynyl, $C_1$–$C_{20}$-alkoxy, $C_1$–$C_{20}$-thioether, $C_1$–$C_{20}$-silyl, $C_1$–$C_{20}$-ester, $C_1$–$C_{20}$-amino, $C_1$–$C_{20}$-fluoroalkyl, and optionally substituted aryl or heteroaryl, $R^4$ and $R^5$ are selected from H, halogen, $C_1$–$C_{20}$-alkyl that is optionally substituted with one or more fluorine atoms, $C_1$–$C_{20}$-alkenyl, $C_1$–$C_{20}$-alkynyl, $C_1$–$C_{20}$-alkoxy, $C_1$–$C_{20}$-thioether, $C_1$–$C_{20}$-silyl, $C_1$–$C_{20}$-ester, $C_1$–$C_{20}$-amino, $C_1$–$C_{20}$-fluoroalkyl, and optionally substituted aryl or heteroaryl, in particular from H, halogen, $C_1$–$C_{20}$-alkyl and $C_1$–$C_{20}$-alkoxy, Y and Z are optionally substituted arylene or heteroarylene, Y and Z are —$CX^1$=$CX^2$— or —C≡C—, in at least one monomer unit $(Y)_a$-$(D)_b$-$(Z)_c$ a, b and c are 1, and one of Y and Z is arylene or heteroarylene and the other is —$CX^1$=$CX^2$— or —C≡C—, if n=b=1 and a=c=0, at least one of $R^2$ and $R^3$ is different from H, if n=b=1 and a=c=0, at least one of $R^4$ and $R^5$ is different from H, n>1.

A further preferred embodiment of the present invention relates to mono-, oligo- and polydithienopyridines that are mesogenic or liquid crystalline, in particular those comprising one or more polymerisable groups. Very preferred materials of this type are monomers and oligomers of formula I1 wherein n is an integer from 1 to 15 and $R^4$ and/or $R^5$ denote P-Sp-X.

These materials are particularly useful as semiconductors or charge transport materials, as they can be aligned into uniform highly ordered orientation in their liquid crystal phase by known techniques, thus exhibiting a higher degree of order that leads to particularly high charge carrier mobility. The highly ordered liquid crystal state can be fixed by in situ polymerisation or crosslinking via the groups P to yield polymer films with high charge carrier mobility and high thermal, mechanical and chemical stability.

It is also possible to copolymerise the polymerisable mono-, oligo- and polydithienopyridines with other polymerisable mesogenic or liquid crystal monomers that are known from prior art, in order to induce or enhance liquid crystal phase behaviour.

Thus, another feature of the invention is a polymerisable liquid crystal material comprising one or more mono-, oligo- or polydithienopyridines comprising at least one polymerisable group, and optionally comprising one or more further polymerisable compounds, wherein at least one of the polymerisable mono-, oligo- and polydithienopyridines and/or of the further polymerisable compounds is mesogenic or liquid crystalline.

Particularly preferred are liquid crystal materials having a nematic and/or smectic phase. For FET applications smectic materials are especially preferred. For OLED applications nematic or smectic materials are especially preferred.

Another feature of the present invention is an anisotropic polymer film with charge transport properties obtainable from a polymerisable liquid crystal material as defined above that is aligned in its liquid crystal phase into macroscopically uniform orientation and polymerised or crosslinked to fix the oriented state.

Another feature of the invention is a liquid crystal side chain polymer (SCLCP) obtained from a polymerisable liquid crystal material as defined above by polymerisation or polymeranaloguous reaction. Particularly preferred are SCLCPs obtained from one or more monomers according to formula I1 wherein one or both of $R^4$ and $R^5$ are a polymerisable or reactive group, or from a polymerisable mixture comprising one or more of such monomers of formula I1.

Another feature of the invention is an SCLCP obtained from one or more monomers of formula I1 wherein one or both of $R^4$ and $R^5$ are a polymerisable group, or from a polymerisable liquid crystal mixture as defined above, by copolymerisation or polymeranaloguous reaction together with one or more additional mesogenic or non-mesogenic comonomers.

Side chain liquid crystal polymers or copolymers (SCLCPs), in which the semiconducting component is located as a pendant group, separated from a flexible backbone by an aliphatic spacer group, offer the possibility to obtain a highly ordered lamellar like morphology. This structure consists of closely packed conjugated aromatic mesogens, in which very close (typically <4 Å) pi-pi stacking can occur. This stacking allows intermolecular charge transport to occur more easily, leading to high charge carrier mobilities. SCLCPs are advantageous for specific applications as they can be readily synthesized before processing and then e.g. be processed from solution in an organic solvent. If SCLCPs are used in solutions, they can orient spontaneously when coated onto an appropriate surface and when at their mesophase temperature, which can result in large area, highly ordered domains.

Especially preferred are mono-, oligo- and polydithienopyridines of the following formulae

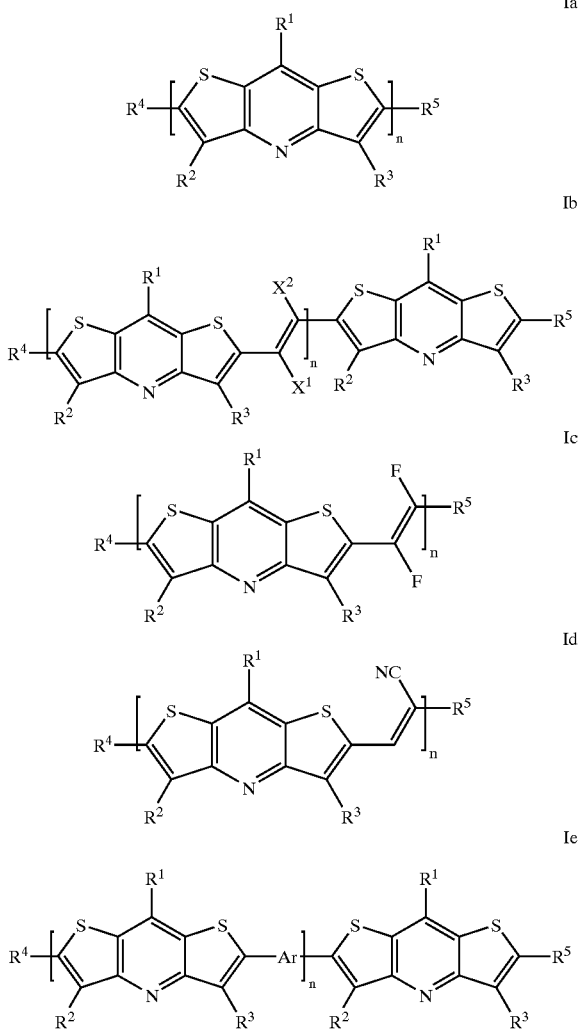

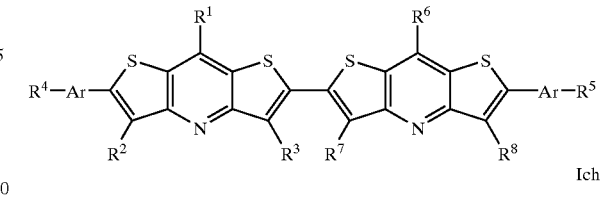

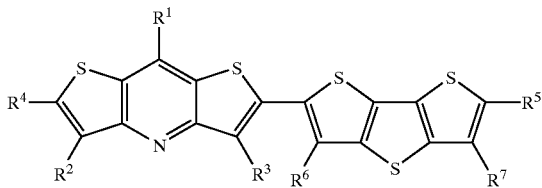

wherein $R^1$, $R^2$ and $R^3$ have the meanings given in formula I, $R^4$ and $R^5$ have one of the meanings of $R^1$, Ar is arylene or heteroarylene, and n is an integer from 1 to 5000.

In these preferred formulae, $R^1$ to $R^5$ are very preferably H, F or alkyl with 1–16 C atoms that is optionally fluorinated, and Ar is very preferably 1,4-phenylene, alkoxyphenylene, alkylfluorene, thiophene-2,5-diyl, thienothiophene-2,5-diyl or dithienothiophene-2,6-diyl.

—$CX^1$—$CX^2$— in these preferred formulae is preferably —CH═CH—, —CH═CF—, —CF═CH—, —CF═CF—, —CH═C(CN)— or —C(CN)═CH—.

Further preferred are polymerisable oligomers of the following formulae wherein $R^1$ to $R^3$ have the meanings of formula I, $R^6$ to $R^8$ have independently of each other one of the meanings of $R^1$, one of $R^4$ and $R^5$ is P-Sp-X and the other is P-Sp-X or has one of the meanings of $R^1$ in formula I1, and Ar is arylene or heteroarylene.

In these preferred formulae, $R^1$ to $R^3$ and $R^6$ to $R^8$ are very preferably H, F or alkyl with 1–6 C atoms that is optionally fluorinated, Ar is very preferably 1,4-phenylene, alkoxyphenylene, alkylfluorene or thiophene-2,5-diyl, and preferably both $R^4$ and $R^5$ are P-Sp-X wherein X is especially preferably a single bond.

Aryl and heteroaryl preferably denote a mono-, bi- or tricyclic aromatic or heteroaromatic with up to 25 C atoms, wherein the rings may be condensed, i.e. fused, in which the heteroaromatic groups contain at least one hetero ring atom, preferably selected from N, O and S. The aryl and heteroaryl groups are optionally substituted with one or more halogen, CN, and/or straight chain, branched or cyclic alkyl having 1 to 20 C atoms, which is unsubstituted, mono- or poly-substituted by F, Cl, Br, I, or —CN, and in which one or more non-adjacent $CH_2$ groups are optionally replaced, in each case independently from one another, by —O—, —S—, —NH—, —$NR^o$—, —$SiR^oR^{oo}$—, —CO—, —COO—, —OCO—, —OCO—O—, —S—CO—, —CO—S—, —CH═CH— or —C≡C— in such a manner that O and/or S atoms are not linked directly to one another.

Especially preferred aryl and heteroaryl groups are phenyl in which, in addition, one or more CH groups may be replaced by N, naphthalene, thiophene, thienothiophene, dithienothiophene, alkyl fluorene and oxazole, all of which can be unsubstituted, mono- or polysubstituted with L, wherein L is halogen or an alkyl, alkoxy, alkylcarbonyl or alkoxycarbonyl group with 1 to 12 C atoms, wherein one or more H atoms may be replaced by F or Cl.

Arylene and heteroarylene preferably denote a mono-, bi- or tricyclic divalent aromatic or heteroaromatic group with up to 25 C atoms, wherein the rings may be condensed, i.e. fused, in which the heteroaromatic groups contain at least one hetero ring atom, preferably selected from N, O and S. The arylene and heteroarylene groups are optionally substituted with one or more halogen, CN, and/or straight chain, branched or cyclic alkyl having 1 to 20 C atoms, which is unsubstituted, mono- or poly-substituted by F, Cl, Br, I, or —CN, and in which one or more non-adjacent $CH_2$ groups are optionally replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CH=CH— or —C≡C— in such a manner that O and/or S atoms are not linked directly to one another.

Especially preferred arylene and heteroarylene groups are 1,4-phenylene in which, in addition, one or more CH groups may be replaced by N, naphthalene-2,6-diyl, thiophene-2,5-diyl, thienothiophene-2,5-diyl, dithienothiophene-2,6-diyl, alkyl fluorene and oxazole, all of which can be unsubstituted, mono- or polysubstituted with L as defined above.

$CX^1=CX^2$ is preferably —CH=CH—, —CH=CF—, —CF=CH—, —CF=CF—, —CH=C(CN)— or —C(CN)=CH—.

If in the formulae shown above and below one of $R^1$ to $R^8$ is an alkyl or alkoxy radical, i.e. where the terminal $CH_2$ group is replaced by —O—, this may be straight-chain or branched. It is preferably straight-chain, has 2 to 8 carbon atoms and accordingly is preferably ethyl, propyl, butyl, pentyl, hexyl, heptyl, octyl, ethoxy, propoxy, butoxy, pentoxy, hexyloxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one $CH_2$ group is replaced by —O—, is preferably straight-chain 2-oxapropyl(=methoxymethyl), 2-(=ethoxymethyl) or 3-oxabutyl(=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-,7-, 8- or 9-oxadecyl, for example.

Fluoroalkyl is preferably $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$.

Halogen is preferably F or Cl.

The polymerisable or reactive group P is preferably selected from $CH_2=CW^1$—COO—,

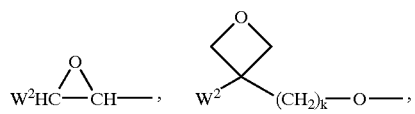

$CH_2=CW^2—(O)_{k1}—$, $CH_3—CH=CH—O—$, $HO—CW^2W^3—$, $HS—CW^2W^3—$, $HW^2N—$, $HO—CW^2W^3—NH—$, $CH_2=CW^1—CO—NH—$, $CH_2=CH—(COO)_{k1}$-Phe-$(O)_{k2}—$, Phe-CH=CH—, HOOC—, OCN— and $W^4W^5W^6Si—$, with $W^1$ being H, Cl, CN, phenyl or alkyl with 1 to 5 C-atoms, in particular H, $C_1$ or $CH_3$, $W^2$ and $W^3$ being independently of each other H or alkyl with 1 to 5 C-atoms, in particular methyl, ethyl or n-propyl, $W^4$, $W^5$ and $W^6$ being independently of each other Cl, oxaalkyl or oxacarbonylalkyl with 1 to 5 C-atoms, Phe being 1,4-phenylene and $k_1$ and $k_2$ being independently of each other 0 or 1.

Especially preferred groups P are $CH_2=CH—COO—$, $CH_2=C(CH_3)—COO—$, $CH_2=CH—$, $CH_2=CH—O—$ and

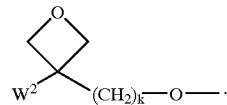

Very preferred are acrylate and oxetane groups. Oxetanes produce less shrinkage upon polymerisation (cross-linking), which results in less stress development within films, leading to higher retention of ordering and fewer defects. Oxetane cross-linking also requires cationic initiator, which unlike free radical initiator is inert to oxygen.

As for the spacer group Sp all groups can be used that are known for this purpose to those skilled in the art. The spacer group Sp is preferably a linear or branched alkylene group having 1 to 20 C atoms, in particular 1 to 12 C atoms, in which, in addition, one or more non-adjacent $CH_2$ groups may be replaced by —O—, —S—, —NH—, —N(CH$_3$)—, —CO—, —O—CO—, —S—CO—, —O—COO—, —CO—S—, —CO—O—, —CH(halogen)-, —C(halogen)$_2$, —CH(CN)—, —CH=CH— or —C≡C—, or a siloxane group.

Typical spacer groups are for example —(CH$_2$)$_p$—, —(CH$_2$CH$_2$O)$_r$—CH$_2$CH$_2$—, —CH$_2$CH$_2$—S—CH$_2$CH$_2$— or —CH$_2$CH$_2$—NH—CH$_2$CH$_2$— or —(SiR⁰R⁰⁰—O)$_p$—, with p being an integer from 2 to 12, r being an integer from 1 to 3 and $R^0$ and $R^{00}$ having the meanings given in formula I.

Preferred spacer groups are ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyliminoethylene, 1-methylalkylene, ethenylene, propenylene and butenylene for example.

Further preferred are compounds with one or two groups P-Sp-X wherein Sp and/or X is a single bond.

In case of compounds with two groups P-Sp-X, each of the two polymerisable groups P, the two spacer groups Sp, and the two linkage groups X can be identical or different.

SCLCPs obtained from the inventive compounds or mixtures by polymerisation or copolymerisation have a backbone that is formed by the polymerisable group P in formula I1.

The mono-, oligo- and polydithienopyridines of the present invention can be synthesized according to or in analogy to known methods. Some preferred methods are described below.

Dithieno[3,2-b:2'3'-e]pyridine (6)

The precursor to dithieno[3,2-b:2'3'-e]pyridine (6) is 3-thiophenamine (4), which can be synthesised for example via the route shown in scheme 1. Saponification of ester (3) and subsequent decarboxylation yields 3-thiophenamine (4) [see reference 10].

Scheme 1:

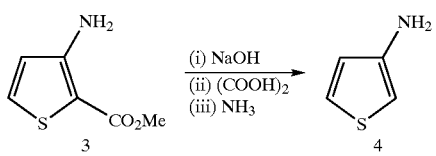

To form dithieno[3,2-b:2'3'-e]pyridine (6), 3-thiophenamine (4) and an aldehyde (5) wherein R is for example an alkyl or fluoroalkyl substituent are stirred together with trifluoroacetic acid in dichloromethane as depicted in scheme 2 [see reference 8]. Using this procedure, various substituents R, like for example alkyl, alkenyl, aryl and heteroaryl groups, can be introduced through modification of the aldehyde (5) employed.

Scheme 2:

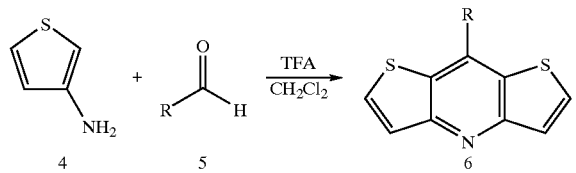

Poly(dithieno[3,2-b:2'3'-e]pyridines) (9)

Poly(dithieno[3,2-b:2'3'-e]pyridines) (9) can be synthesized for example by two routes from dithienopyridine (6) as outlined in scheme 3. Firstly, the direct polymerisation of the dithieno[3,2-b:2'3'-e]pyridine (6) using ferric chloride (oxidative coupling) to yield polymer (9) [see reference 11]. In the second route, dithienopyridine (6) is stannylated at the 2,6-positions by treatment with n-butyllithium followed by trimethyltin chloride to yield bis(trimethylstannyl) dithienopyridine (7), which is seubsequently brominated using N-bromosuccinimide to dibromo dithienopyridine (8). Dibromo dithienopyridine (8) is then polymerised using Ni(cod)$_2$, 1,5-cyclooctadiene and triphenylphosphine (Yamamoto coupling) [see reference 12]. Alternatively, dibromo dithienopyridine (8) is converted to the mono-Grignard and polymerised using Ni(dppp)Cl$_2$ to yield polymer (9) [see reference 13].

Scheme 3:

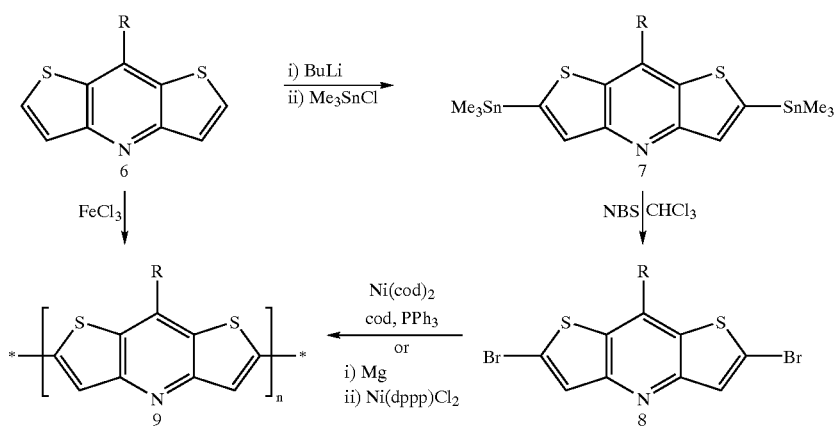

wherein n has the meaning of formula I.

Other coupling routes to polymer (9) are Stille coupling [see reference 14], Rieke coupling [see reference 15], and Suzuki coupling [see reference 16].

Reactive mesogens comprising an oligodithienopyridine group and one or two polymerisable groups P-Sp-X can be prepared for example according to or in analogy to the following synthesis routes.

Bis(dithieno[3,2-b:2'3'-e]pyridine) Reactive Mesogens, Route 1

As depicted in scheme 4 the dimer core (10) is readily formed by mono-lithiation of dithieno[3,2-b:2'3'-e]pyridine (6) with n-BuLi followed by oxidative coupling with a metal salt, for example Fe(acac)$_3$. A similar strategy is involved in the synthesis of BDT (bisdithienothiophene) [see reference 17]. Dimer (10) is stannylated at the 2,2'-positions by treatment with n-buthyllithium followed by trimethyltin chloride to yield (11), which is subsequently brominated using N-bromosuccinimide to (12). This can be cross-coupled with an alkyl zinc reagent in the presence of a nickel catalyst to yield (13) [see reference 18]. Many organozinc reagents are commercially available or are readily prepared form the corresponding alkyl iodide. Routine methodology converts the bis-alkyl alcohol or chloride into the bis-acrylate or bis-oxetane.

Scheme 4:

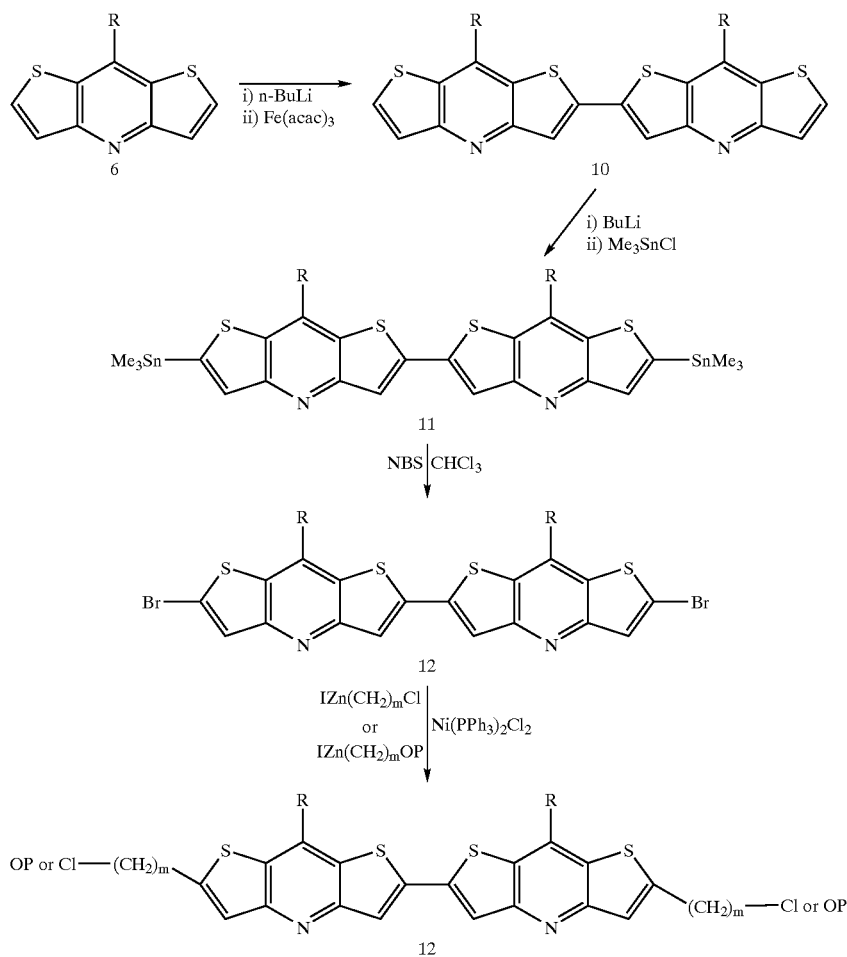

wherein m is an integer e.g. from 1 to 20 and P is a protecting group.

Bis(dithieno[3,2-b:2'3'-e]pyridine) reactive mesogens. Route 2

According to scheme 5, dithienopyridine (6) is stannylated at the 2,6-positions by treatment with n-butyllithium followed by trimethyltin chloride to yield bis(trimethylstannyl) dithienopyridine (7), which is subsequently brominated using N-bromosuccinimide to dibromo dithienopyridine (8). Cross-coupling of the dibromo dithienopyridine (8) with an alkyl Grignard reagent in the presence of a nickel catalyst yields mono-alkyl alcohol (14). Homocoupling of the Grignard reagent of mono-alkyl alcohol in the presence of a nickel catalyst yields bis-alkyl alcohol (13). Routine methodology converts the bis-alkyl alcohol into the bis-acrylate or bis-oxetane.

Scheme 5:

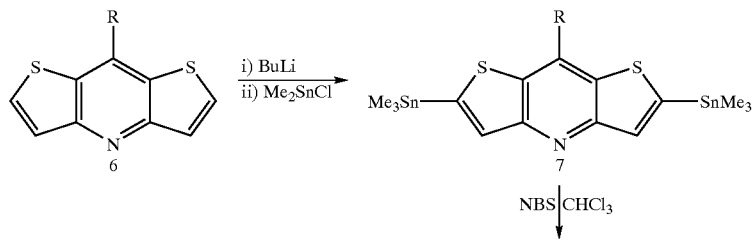

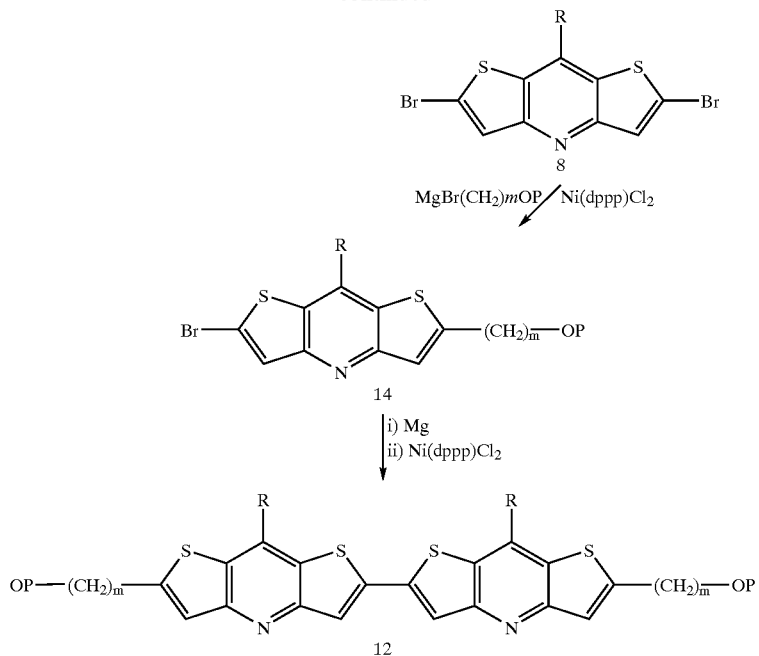

wherein m is an integer e.g. from 1 to 20 and P is a protecting group.

Dithieno[3,2-b:2'3'-e]pyridine Polymers Containing Conjugated Groups $CX^1=CX^2$ or Ar The Stille coupling of dibromo DTP (8) with the bis-organotin reagent (15) yields polymer (16) containing $CX^1=CX^2$ groups [see reference 20].

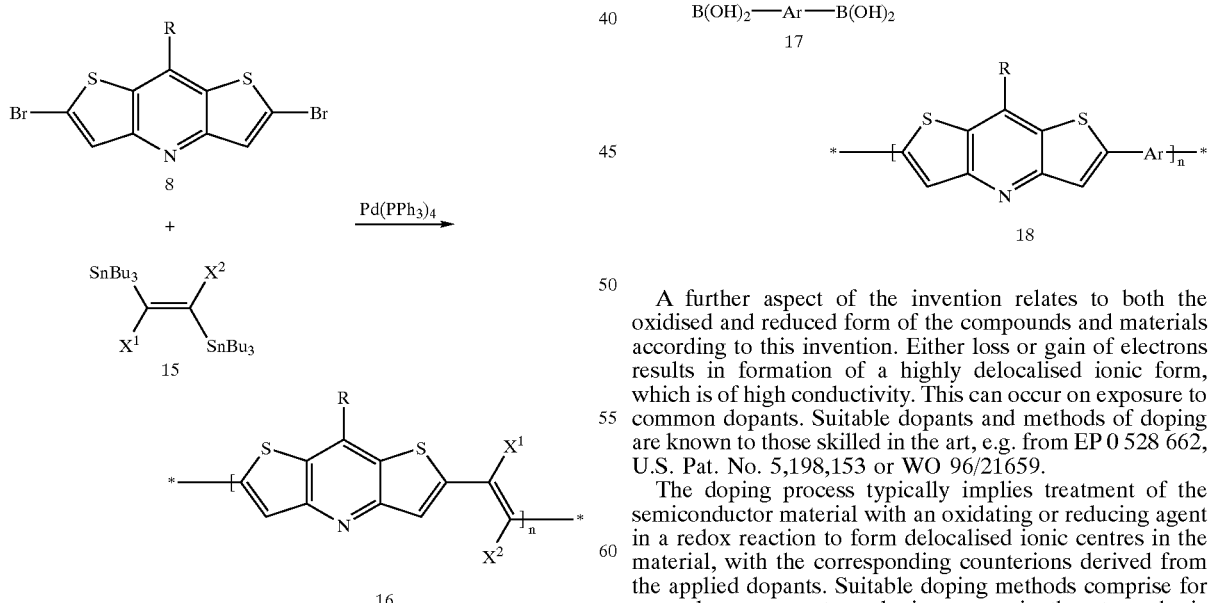

The Suzuki coupling of dibromo DTP (8) with bis-boronic acid (17) yields polymer (18) containing aryl groups.

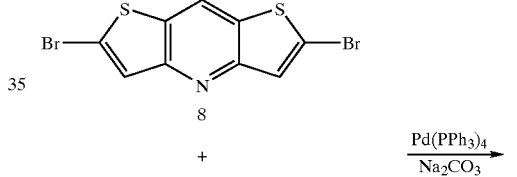

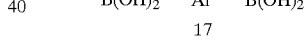

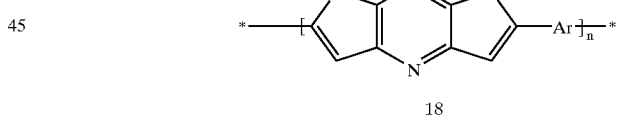

A further aspect of the invention relates to both the oxidised and reduced form of the compounds and materials according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g. $I_2$, $Cl_2$, $Br_2$, ICl, $ICl_3$, IBr and IF), Lewis acids (e.g. $PF_5$, $AsF_5$, $SbF_5$, $BF_3$, $BCl_3$, $SbCl_5$, $BBr_3$ and $SO_3$), protonic acids, organic acids, or amino acids (e.g. HF, HCl, $HNO_3$, $H_2SO_4$, $HClO_4$, $FSO_3H$ and $ClSO_3H$), transition metal compounds (e.g. $FeCl_3$, FeOCl, $Fe(ClO_4)_3$, $Fe(4—CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g. $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g. $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Br), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds and materials of the present invention can be used as an organic "metal" in applications, for example, but not limited to, charge injection layers and ITO planarising layers in organic light emitting diode applications, films for flat panel displays and touch screens, antistatic films, printed conductive substrates, patterns or tracts in electronic applications such as printed circuit boards and condensers.

Mono-, oligo- and polymers according to the present invention that comprise one or more groups P-Sp-X can be polymerised, or copolymerised with other polymerisable compounds, via the polymerisable group P. This is preferably done by in-situ polymerisation of a coated layer of the material, preferably during fabrication of the electronic or optical device comprising the inventive semiconductor material. In case of liquid crystal materials, these are preferably aligned in their liquid crystal state into homeotropic orientation prior to polymerisation, where the conjugated pi-electron systems are orthogonal to the direction of charge transport. This ensures that the intermolecular distances are minimised and hence then energy required to transport charge between molecules is minimised. The molecules are then polymerised or crosslinked to fix the uniform orientation of the liquid crystal state. Alignment and curing are carried out in the liquid crystal phase or mesophase of the material. This technique is known in the art and is generally described for example in D. J. Broer, et al., Angew. Makromol. Chem. 183, (1990), 45–66.

Alignment of the liquid crystal material can be achieved for example by treatment of the substrate onto which the material is coated, by shearing the material during or after coating, by application of a magnetic or electric field to the coated material, or by the addition of surface-active compounds to the liquid crystal material. Reviews of alignment techniques are given for example by 1. Sage in "Thermotropic Liquid Crystals", edited by G. W. Gray, John Wiley & Sons, 1987, pages 75–77, and by T. Uchida and H. Seki in "Liquid Crystals—Applications and Uses Vol. 3", edited by B. Bahadur, World Scientific Publishing, Singapore 1992, pages 1–63. A review of alignment materials and techniques is given by J. Cognard, Mol. Cryst. Liq. Cryst. 78, Supplement 1-(1981), pages 1–77.

Polymerisation takes place by exposure to heat or actinic radiation. Actinic radiation means irradiation with light, like UV light, IR light or visible light, irradiation with X-rays or gamma rays or irradiation with high energy particles, such as ions or electrons. Preferably polymerisation is carried out by UV irradiation at a non-absorbing wavelength. As a source for actinic radiation for example a single UV lamp or a set of UV lamps can be used. When using a high lamp power the curing time can be reduced. Another possible source for actinic radiation is a laser, like e.g. a UV laser, an IR laser or a visible laser.

Polymerisation is preferably carried out in the presence of an initiator absorbing at the wavelength of the actinic radiation. For example, when polymerising by means of UV light, a photoinitiator can be used that decomposes under UV irradiation to produce free radicals or ions that start the polymerisation reaction. When curing polymerisable materials with acrylate or methacrylate groups, preferably a radical photoinitiator is used, when curing polymerisable materials with vinyl, epoxide and oxetane groups, preferably a cationic photoinitiator is used. It is also possible to use a polymerisation initiator that decomposes when heated to produce free radicals or ions that start the polymerisation. As a photoinitiator for radical polymerisation for example the commercially available Irgacure 651, Irgacure 184, Darocure 1173 or Darocure 4205 (all from Ciba Geigy AG) can be used, whereas in case of cationic photopolymerisation the commercially available UVI 6974 (Union Carbide) can be used.

The polymerisable material can additionally comprise one or more other suitable components such as, for example, catalysts, sensitizers, stabilizers, inhibitors, chain-transfer agents, co-reacting monomers, surface-active compounds, lubricating agents, wetting agents, dispersing agents, hydrophobing agents, adhesive agents, flow improvers, defoaming agents, deaerators, diluents, reactive diluents, auxiliaries, colourants, dyes or pigments.

Mono-, oligo- and polymers comprising one or more groups P-Sp-X can also be copolymerised with polymerisable mesogenic compounds to induce, or, in case of mesogenic materials of formula I, enhance liquid crystal phase behaviour. Polymerisable mesogenic compounds that are suitable as comonomers are known in prior art and disclosed for example in WO 93/22397; EP 0,261,712; DE 195,04,224; WO 95/22586 and WO 97/00600.

SCLCPs can be prepared from the polymerisable compounds or mixtures according to the invention by the methods described above, or by conventional polymerisation techniques which are known to those skilled in the art, including for example radicalic, anionic or cationic chain polymerisation, polyaddition or polycondensation. Polymerisation can be carried out for example as polymerisation in solution, without the need of coating and prior alignment, or polymerisation in situ. It is also possible to form SCLCPs by grafting compounds according to the invention with a suitable reactive group, or mixtures thereof, to presynthesized isotropic or anisotropic polymer backbones in a polymeranaloguous reaction. For example, compounds with a terminal hydroxy group can be attached to polymer backbones with lateral carboxylic acid or ester groups, compounds with terminal isocyanate groups can be added to backbones with free hydroxy groups, compounds with terminal vinyl or vinyloxy groups can be added e.g. to polysiloxane backbones with Si—H groups. It is also possible to form SCLCPs by copolymerisation or polymeranaloguous reaction from the inventive compounds together with conventional mesogenic or non mesogenic comonomers. Suitable comonomers are known to those skilled in the art. In principle it is possible to use all conventional comonomers known in the art that carry a reactive or polymerisable group capable of undergoing the desired polymer-forming reaction, like for example a polymerisable or reactive group P as defined above. Typical mesogenic comonomers are for example those mentioned in WO 93/22397; EP 0,261,712; DE 195,04,224; WO 95/22586 and WO 97/00600. Typical non mesogenic comonomers are for example alkyl mono- or diacrylates or alkyl mono- or dimethacrylates with alkyl groups of 1 to 20 C atoms, like methyl acrylate or methyl methacrylate, trimethylpropane trimethacrylate or pentaerythritol tetraacrylate.

The mono-, oligo- and polydithienopyridines of the present invention are useful as optical, electronic and semiconductor materials, in particular as charge transport materials in field effect transistors (FETs) e.g. as components of integrated circuitry, ID tags or TFT applications. Alternatively, they may be used in organic light emitting diodes (OLEDs) in electroluminescent display applications or as backlight of e.g. liquid crystal displays, as photovoltaics or sensor materials, for electrophotographic recording, and for other semiconductor applications.

Especially the oligomers and polymers according to the invention show advantageous solubility properties which allow production processes using solutions of these compounds. Thus films, including layers and coatings, may be generated by low cost production techniques e.g. spin coating. Suitable solvents or solvent mixtures comprise alkanes and/or aromatics, especially their fluorinated derivatives.

The materials of the present invention are useful as optical, electronic and semiconductor materials, in particular as charge transport materials in field effect transistors (FETs), as photovoltaics or sensor materials, for electrophotographic recording, and for other semiconductor applications. Such FETs, where an organic semiconductive material is arranged as a film between a gate-dielectric and a drain and a source electrode, are generally known e.g. from U.S. Pat. No. 5,892,244, WO 00/79617, U.S. Pat. No. 5,998,804, and from the references cited in the background and prior art chapter and listed below. Due to the advantages, like low cost production using the solubility properties of the compounds according to the invention and thus the processibility of large surfaces, preferred applications of these FETs are such as integrated circuitry, TFT-displays and security applications.

In security applications, field effect transistors and other devices with semiconductive materials, like transistors or diodes, may be used for ID tags or security markings to authenticate and prevent counterfeiting of documents of value like banknotes, credit cards or ID cards, national ID documents, licenses or any product with money value, like stamps, tickets, shares, cheques etc.

Alternatively, the mono-, oligo- and polymers according to the invention may be used in organic light emitting devices or diodes (OLEDs), e.g. in display applications or as backlight of e.g. liquid crystal displays. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see e.g. Meerholz, Synthetic Materials, 111–112, 2000, 31–34, Alcala, J. Appl. Phys., 88, 2000, 7124–7128 and the literature cited therein.

According to another use, the inventive compounds, materials or films, especially those which show photoluminescent properties, may be employed as materials of light sources, e.g. of display devices such as described in EP 0 889 350 A1 or by C. Weder et al., Science, 279, 1998, 835–837.

REFERENCES

1. H. E. Katz, Z. Bao, S. L. Gilat, *Acc. Chem. Res.*, 2001, 34, 5, 359.
2. Sirringhaus, R. H. Friend, X. C. Li, S. C. Moratti, A. B. Holmes and N. Feeder, *Appl. Phys. Lett.*, 1997, 71, 26, 3871.
3. X. C. Li, H. Sirringhaus, F. Garnier, A. B. Holmes, S. C. Morafti, N. Feeder, W. Clegg, S. J. Teat and R. H. Friend, *J. Am. Chem. Soc.*, 1998, 120, 2206
4. J. J. Morrison, M. M. Murray, X. C. Li, A. B. Holmes, S.C. Moratti, R. H. Friend and H. Sirringhaus, *Synth. Met.*, 1999, 102, 987.
5. Z. Bao, A. Dodabalapur and A. J. Lovinger, *Appl. Phys. Lett.*, 1996, 69, 4108.
6. H. Sirringhaus, N. Tessler, D. S. Thomas, P. J. Brown, R. H. Friend, *Adv. Solid State Phys.*, 1999, 39, 101.
7. F. Jong, M. J. Janssen, *J. Org. Chem.*, 1971, 36, 1645.
8. M. Berkaoui, F. Outurquin and C. Paulmier, *J. Heterocyclic Chem.*, 1996, 33, 9.
9. H. Sirringhaus, R. J. Wilson, R. H. Friend, M. Inbasekaran, W. Wu, E. P. Woo, M. Grell, D. D. C. Bradley, *Appl. Phys. Lett.*, 2000, 77, 3, 406.
10. J. M. Barker, P. R. Huddleston and M. L. Wood, *Synth. Comm.*, 1995, 25, 23, 3729.
11. K. Yoshino, S. Hayashi and R. Sugimoto, *Jpn. J. Appl. Phys.*, 1984, 23, L899.
12. T. Yamamoto, A. Morita, Y. Miyazaki, T. Maruyama, H. Wakayama, Z. H. Zhou, Y. Nakamura, T. Kanbara, S. Sasaki and K. Kubota, *Macromolecules*, 1992, 25, 1214.
13. R. D. McCullough, R. D. Lowe, *J. Chem. Soc., Chem. Commun.*, 1992, 70.
14. D. Milstein, J. K. Stille, *J. Am. Chem. Soc.*, 1979, 101, 4992.
15. T.-A. Chen, R. D. Rieke, *J. Am. Chem. Soc.*, 1992, 114, 10087.
16. N. Miyaura, T. Yanagi, A. Suzuki, *Synth. Commun.*, 1981, 11, 513.
17. L. Xiao-Chang, H. Sirringhaus, F. Garnier, A. B. Holmes, S. C. Moratti, N. Feeder, W. Clegg, S. J. Teat, R. H. Friend, *J. Am. Chem. Soc.*, 1998, 120, 2206.
18. B. H. Lipshutz, P. A. Blomgren, S. K. Kim, *Tetrahedron Lett.*, 1999, 40, 2, 197.
19. R. S. Loewe, R. D. McCullough, *Chem. Mater.*, 2000, 12, 3214.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all cited applications, patents and publications, and corresponding European Patent application No. 01115743.5, filed Jul. 9, 2001, are hereby incorporated by reference.

EXAMPLE 1

4-Hexyldithieno[3,2-b:2'3'-e]pyridine (1) was prepared as described below.

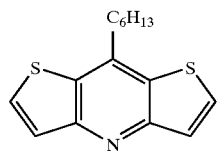

(1)

A solution of heptanal (0.59 g, 5.16 mmol) and trifluoroacetic acid (100 mg) in anhydrous dichloromethane (50 mL) was added dropwise to a solution of 3-aminothiophene (0.93 g, 9.38 mmol) in anhydrous dichloromethane (50 mL) at −5° C. The reaction mixture was stirred at room temperature for 1.5 h. Trifluoroacetic acid (1.07 g, 9.38 mmol) was added and the reaction mixture was then heated at reflux for 6 h. The solution was cooled and diethyl ether (150 mL) and water (30 mL) were added. The aqueous layer was basified with 0.5 N aqueous sodium hydroxide solution. The organic layer was separated. The aqueous layer was again extracted into diethyl ether (150 mL). The combined organic extracts were dried over sodium sulfate and concentrated in vacuo. Purification by flash chromatography (eluent: 90% petroleum ether 80–100/10% dichloromethane to 100% dichloromethane) afforded 4-hexyldithieno[3,2-b:2'3'-e]pyridine (0.58 g, 45%) as a red oil: $\delta_H$(CDCl$_3$, 250 MHz) 7.75 (2H, d, $^3J_{HH}$=6 Hz), 7.59 (2H, d, $^3J_{HH}$=6 Hz), 3.16 (2H, t, $^3J_{HH}$=8 Hz), 1.90 (2H, m), 1.27–1.49 (6H, m), 0.89 (3H, t, $^3J_{HH}$=7 Hz); $\delta_C$(CDCl$_3$, 63 MHz) 156.2, 140.4, 130.7, 129.7, 34.8, 31.9, 29.8, 28.3, 22.9, 14.4.

EXAMPLE 2

4-Dodecyldithieno[3,2-b:2'3'-e]pyridine (2) was prepared as described below.

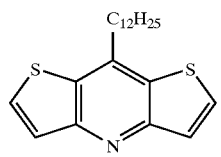

(2)

A solution of tridecanal (25.00 g, 126.04 mmol) and trifluoroacetic acid (2.00 g) in anhydrous dichloromethane (200 mL) was added dropwise to a solution of 3-aminothiophene (21.00 g, 211.78 mmol) in anhydrous dichloromethane (200 mL) at −10° C. The reaction mixture was stirred at room temperature for 1.5 h. Trifluoroacetic acid (24.15 g, 211.78 mmol) was added and the reaction mixture was then heated at reflux for 24 h. The solution was cooled and diethyl ether (300 mL) and water (100 mL) were added. The aqueous layer was basified with 0.5 N aqueous sodium hydroxide solution. The organic layer was separated. The aqueous layer was again extracted into diethyl ether (2×100 mL). The combined organic extracts were dried over sodium sulfate and concentrated in vacuo. Purification by flash chromatography (eluent: dichloromethane) afforded 4-dodecyldithieno[3,2-b:2'3'-e]pyridine (16.74 g, 22%) as a red oil: $\delta_H$(CDCl$_3$, 300 MHz) 7.76 (2H, d, $^3J_{HH}$=6 Hz), 7.60 (2H, d, $^3J_{HH}$=6 Hz), 3.15 (2H, t, $^3J_{HH}$=7.5 Hz), 1.90 (2H, m), 1.25–1.50 (18H, m), 0.88 (3H, t, $^3J_{HH}$=7.5 Hz); $\delta_C$(CDCl$_3$, 75 MHz) 155.8, 140.0, 130.3, 129.4, 125.3, 34.5, 31.9, 29.7, 29.6, 29.5, 29.4, 28.0, 22.7, 14.1.

EXAMPLE 3

2,6-Dibromo-4-hexyldithieno[3,2-b:2'3'-e]pyridine (3) was prepared as described below.

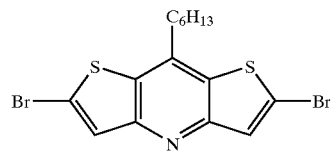

(3)

A 2.5 M solution of butyllithium in hexanes (7.0 mL, 17.50 mmol) was added to a solution of 4-hexyldithienopyridine (1) (2.00 g, 7.26 mmol) in anhydrous tetrahydrofuran (30 mL) at −78° C. The solution was stirred at −78° C. for 1 h, then at 0° C. for 5 h. The solution was cooled back down to −78° C. and a solution of trimethyltin chloride (2.89 g, 14.52 mmol) in anhydrous tetrahydrofuran (20 mL) was added dropwise. The reaction was stirred overnight for 22 h and allowed to attain room temperature. The reaction mixture was poured onto ice (50 mL) and extracted into diethyl ether (2×100 mL). The combined extracts were washed with 3% aqueous ammonia solution (100 mL) and water (100 mL), then dried over sodium sulfate and concentrated in vacuo to yield a dark red oil. Kugelrohr distillation was used to remove some impurities from the bis(trimethylstannyl) intermediate, however the pure material was not isolated.

N-Bromosuccinimide (1.54 g, 8.65 mmol) was added to a solution of the crude bis(trimethylstannyl) intermediate (2.60 g) in chloroform (20 mL). The reaction mixture was stirred at room temperature for 1.5 h. The reaction mixture was poured into water (25 mL) and extracted into diethyl ether (2×100 mL). The combined extracts were dried over sodium sulfate and concentrated in vacuo to yield an pale orange solid. Recrystallisation twice from diethyl ether yielded 2,6-dibromo-4-hexyldithieno[3,2-b:2'3'-e]pyridine (3) (0.82 g, 1.89 mmol, 26%) as fine white needles: mp. 123–125° C.; $\delta_H$(CDCl$_3$, 400 MHz) 7.56 (2H, s), 2.96 (2H, t, $^3J_{HH}$=7.5 Hz), 1.82 (2H, m), 1.25–1.45 (6H, m), 0.90 (3H, t, $^3J_{HH}$=7.5 Hz); $\delta_C$(CDCl$_3$, 100 MHz) 154.8, 138.0, 131.2, 127.8, 120.8, 34.3, 31.4, 29.3, 27.1, 22.4, 14.0.

EXAMPLE 4

2,6-Dibromo-4-dodecyldithieno[3,2-b:2'3'-e]pyridine (4) was prepared as described below.

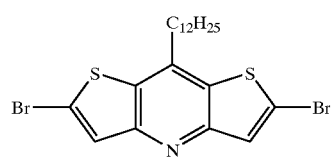

(4)

A 2.5 M solution of butyllithium in hexanes (21.0 mL, 52.50 mmol) was added to a solution of 4-dodecyldithienopyridine (2) (7.76 g, 21.58 mmol) in anhydrous tetrahydrofuran (60 mL) at −78° C. The solution was stirred at −78° C. for 1 h, then at 0° C. for 5 h. The solution was cooled back down to −78° C. and a solution of trimethyltin chloride (8.60 g, 43.16 mmol) in anhydrous tetrahydrofuran (40 mL) was added dropwise. The reaction was stirred overnight for 17 h and allowed to attain room temperature. The reaction mixture was poured onto ice (50 mL) and extracted into diethyl ether (2×100 mL). The combined extracts were washed with 3% aqueous ammonia solution (100 mL) and water (100 mL), then dried over sodium sulfate and concentrated in vacuo to yield a brown oil. The crude material was filtered through a pad of silica (eluent: 50% dichloromethane/50% petroleum ether 40–60) in order to remove some impurities from the bis (trimethylstannyl) intermediate, however the pure material was not isolated.

N-Bromosuccinimide (2.70 g, 15.18 mmol) was added to a solution of the crude bis(trimethylstannyl) intermediate (5.20 g) in chloroform (100 mL). The reaction mixture was stirred at room temperature for 6 h. The reaction mixture was poured into water (50 mL) and extracted into diethyl ether (2×100 mL). The combined extracts were dried over sodium sulfate and concentrated in vacuo to yield an orange solid. Purification by flash chromatography (eluent: 50% dichloromethane/50% petroleum ether 40–60) followed by recrystallisation from absolute ethanol yielded 2,6-dibromo-4-dodecyldithieno[3,2-b:2'3'-e]pyridine (4) (0.72 g, 1.39 mmol, 6%) as white crystals: mp. 82–83° C.; $\delta_H$(CDCl$_3$, 300 MHz) 7.57 (2H, s), 2.98 (2H, t, $^3J_{HH}$=7.5 Hz), 1.83 (2H, m), 1.25–1.50 (18H, m), 0.88 (3H, t, $^3J_{HH}$=7.5 Hz); $\delta_C$(CDCl$_3$, 75 MHz) 154.9, 138.1, 131.2, 127.9, 120.8, 34.3, 31.9, 29.6, 29.4, 29.3, 27.8, 22.7, 14.1.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An oligo- or a polymer comprising at least one recurring polymerizable dithieno[3,2-b;2',3']pyridine group.

2. An oligo- or a polymer according to claim 1, further comprising at least one reactive group capable of a crosslinking reaction.

3. An oligo- or a polymer according to claim 1, which exhibits mesogenic or liquid crystalline properties.

4. A oligo- or a polymer according to claim 1 comprising at least two recurring units, wherein at least one recurring unit comprises one or more dithieno[3,2-b;2',3']pyridine groups.

5. A polymerisable liquid crystal material comprising at least one oligo- or polymer according to claim 1 comprising at least one polymerisable group, and optionally at least one polymerisable compound, wherein at least one of said oligo- or polymer and/or said further polymerisable compound has mesogenic or liquid crystalline properties.

6. An anisotropic polymer film with charge transport properties made from a polymerisable liquid crystal material according to claim 5 wherein the polymerisable liquid crystal material is aligned in its liquid crystal phase into macroscopically uniform orientation and polymerised or crosslinked to fix the oriented state.

7. A side chain liquid crystal polymer made by polymerizing one or more oligomers or polymers according to claim 1 optionally with one or more additional mesogenic or non-mesogenic comonomers.

8. A semiconductor or a charge transport material in an optical, an electrooptical or an electronic device, a component of integrated circuitry, a field effect transistor, a RFID tag, a semiconducting component for organic light emitting diode, an electroluminescent display device, a backlight, a photovoltaic, a sensor device, or an electrophotographic recording device comprising an oligo- or a polymer according to claim 1.

9. A security marking or device comprising at least an oligo- or a polymer of claim 1.

10. A process for making a conducting ionic species comprising oxidatively or reductively doping an oligo- or a polymer, according to claim 1.

11. A charge injection layer, a planarising layer, an antistatic film, a conducting substrate, a pattern for an electronic application, or a flat panel display, comprising an oligo- or a polymer according to claim 1.

12. A side chain liquid polymer made by grafting one or more oligomers or polymers according to claim 1 to a polymer backbone in a polymer analogous reaction, optionally with one or more additional mesogenic or non-mesogenic comonomers.

13. A mono-, an oligo- or a polymer comprising one or more identical or different recurring units of formula I

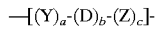

wherein

D is a dithienopyridine group of formula II

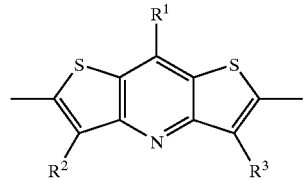

R$^1$–R$^3$ are, independently of each other, H, halogen or straight chain, branched or cyclic alkyl with 1–20 C-atoms, which may be unsubstituted, mono- or polysubstituted by F, Cl, Br, I or CN, optionally one or more non-adjacent CH$_2$ groups are replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, R$^0$ and R$^{00}$ are, independently of each other, H or alkyl with 1–12 C-atoms, Y and Z are, independently of each other, —CX$^1$=CX$^2$—, —C≡C—, or optionally substituted arylene or heteroarylene, X$^1$ and X$^2$ are, independently of each other, H, F, Cl or CN, and a, b and c are, independently of each other, 0 or 1, with a+b+c>0, and wherein in at least one recurring unit b is 1, and if b=1 and a=c=0, at least one of R$^2$ and R$^3$ is different from H.

14. A mono-, an oligo- or a polymer according to claim 13, of formula I1

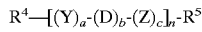

wherein

D is a dithienopyridine group of formula II

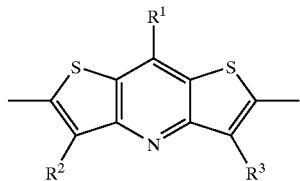

R$^1$–R$^3$ are, independently of each other, H, halogen or straight chain, branched or cyclic alkyl with 1–20 C-atoms, which may be unsubstituted, mono- or poly-substituted by F, Cl, Br, I or CN, optionally one or more non-adjacent CH$_2$ groups is replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, R$^0$ and R$^{00}$ are, independently of each other, H or alkyl with 1–12 C-atoms, Y and Z are, independently of each other, —CX$^1$=CX$^2$—, —C≡C—, or optionally substituted arylene or heteroarylene, X$^1$ and X$^2$ are, independently of each other, H, F, Cl or CN, and a, b and c are, independently of each other, 0 or 1, with a+b+c>0, and wherein at least one recurring unit b is 1, n is an integer 1–5000, R$^4$ and R$^5$ are, independently of each other, H, halogen, Sn(R$^0$)$_3$ or straight chain, branched or cyclic alkyl with 1–20 C-atoms, which may be unsubstituted, mono- or poly-substituted by F, Cl, Br, I or CN, optionally one or more non-adjacent CH$_2$ groups are replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, or denote P-Sp-X, P is a polymerisable or reactive group, Sp is a spacer group or a single bond, and X is —O—, —S—, —OCH$_2$—, —CH$_2$O—, —CO—, —COO—, —OCO—, —OCO—O—, —CO—NR$^0$—, —NR$^0$—CO—, —OCH$_2$—, —CH$_2$O—, —SCH$_2$—, —CH$_2$S—, —CH=CH—COO—, —OOC—CH=CH— or a single bond, and wherein the recurring units [(Y)$_a$-(D)$_b$-(Z)$_c$] can be identical or different.

15. A mono-, an oligo- or a polymer according to claim 14, wherein n is an integer 1–15 and one or both of R$^4$ and R$^5$ denote P-Sp-X.

16. A mono-, an oligo- or a polymer according to claim 14, wherein P is CH$_2$=CW$^1$—COO—,

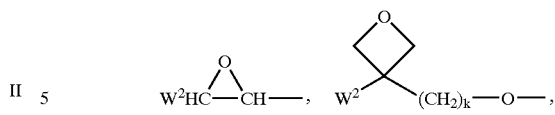

CH$_2$=CW$^2$—(O)$_{k1}$—, CH$_3$—CH=CH—O—, HO—CW$^2$W$^3$—, HS—CW$^2$W$^3$—, HW$^2$N—, HO—CW$^2$W$^3$—NH—, CH$_2$=CW$^1$—CO—NH—, CH$_2$=CH—(COO)$_{k1}$-Phe-(O)$_{k2}$—, Phe-CH=CH—, HOOC—, OCN— or W$^4$W$^5$W$^6$Si—, with W$^1$ being H, Cl, CN, phenyl or alkyl with 1–5 C-atoms, W$^2$ and W$^3$ being independently of each other H or alkyl with 1–5 C-atoms, W$^4$, W$^5$ and W$^6$ are, independently of each other, Cl, oxaalkyl or oxacarbonylalkyl with 1–5 C-atoms, Phe being 1,4-phenylene and k1 and k2 being independently of each other 0 or 1.

17. A mono-, an oligo- or a polymer according to claim 16, wherein W$^1$ is H, Cl, or CH$_3$.

18. An oligo- or a polymer according to claim 14, wherein n is an integer 2–5000 and R$^4$ and R$^5$ are, independently of each other, H, halogen or straight chain, branched or cyclic alkyl with 1–20 C-atoms, which may be unsubstituted, mono- or poly-substituted by F, Cl, Br, I or CN, optionally one or more non-adjacent CH$_2$ groups are replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl.

19. A mono-, an oligo- or a polymer according to claim 14 of the formula

Ia

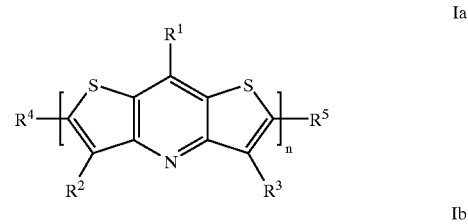

Ib

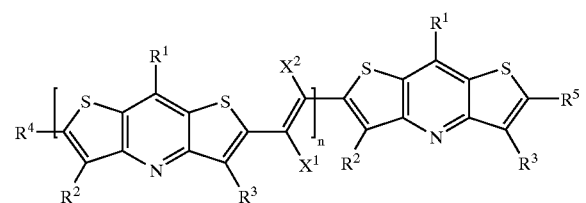

Ic

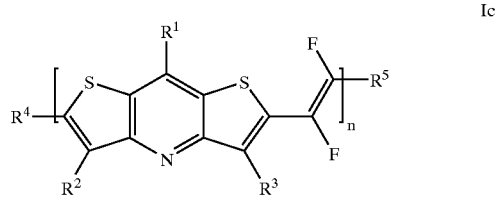

-continued

Id

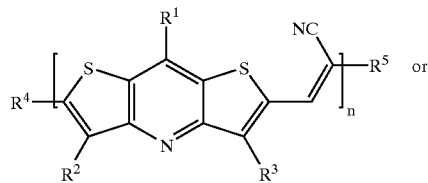

Ie

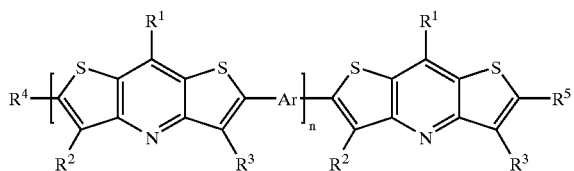

wherein R¹–R⁵ are, independently of each other, H, halogen or straight chain, branched or cyclic alkyl with 1–20 C-atoms, which may be unsubstituted, mono- or poly-substituted by F, Cl, Br, I or CN, optionally one or more non-adjacent CH₂ groups are replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, R⁰ and R⁰⁰ are, independently of each other, H or alkyl with 1–12 C-atoms, Ar is a bivalent mono-, bi- or tricyclic aromatic or heteroaromatic group with up to 25 C atoms optionally comprising condensed rings and optionally substituted with one or more groups independently of each other, H, halogen or straight chain, branched or cyclic alkyl with 1–20 C-atoms, which may be unsubstituted, mono- or poly-substituted by F, Cl, Br, I or CN, optionally one or more non-adjacent CH₂ groups are replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, R⁰ and R⁰⁰ are, independently of each other, H or alkyl with 1–12 C-atoms, and n is an integer of 1–5000.

20. An oligomer according to claim 14, of the formula

If

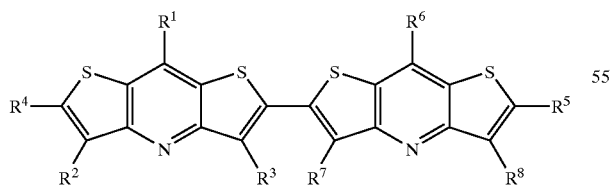

Ig

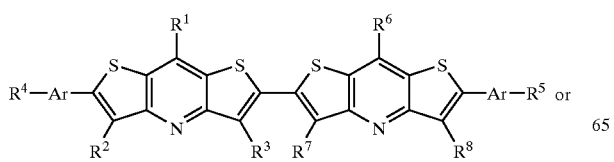

-continued

Ih

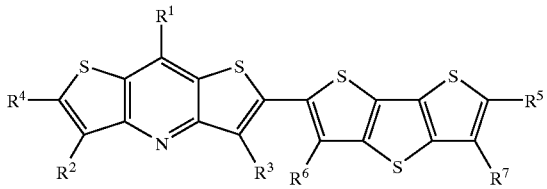

wherein R¹–R³ and R⁶–R⁸ are, independently of each other, H, halogen or straight chain, branched or cyclic alkyl with 1–20 C-atoms, which may be unsubstituted, mono- or poly-substituted by F, Cl, Br, I or CN, optionally one or more non-adjacent CH₂ groups are replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, R⁰ and R⁰⁰ are, independently of each other, H or alkyl with 1–12 C-atoms, one of R⁴ and R⁵ is P-Sp-X and the other is P-Sp-X or are, independently of each other, H, halogen or straight chain, branched or cyclic alkyl with 1–20 C-atoms, which may be unsubstituted, mono- or poly-substituted by F, Cl, Br, I or CN, optionally one or more non-adjacent CH₂ groups is replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, R⁰ and R⁰⁰ are, independently of each other, H or alkyl with 1–12 C-atoms, and Ar is a bivalent mono-, bi- or tricyclic aromatic or heteroaromatic group with up to 25 C atoms that may also comprise condensed rings and is optionally substituted with one, or more groups independently of each other, H, halogen or straight chain, branched or cyclic alkyl with 1–20 C-atoms, which may be unsubstituted, mono- or poly-substituted by F, Cl, Br, I or CN, optionally one or more non-adjacent CH₂ groups are replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, and R⁰ and R⁰⁰ are, independently of each other, H or alkyl with 1–12 C-atoms.

21. A monomer according to claim 13, of the formula (3)

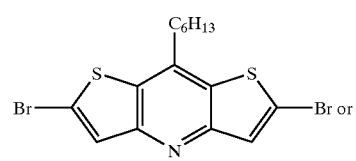

(4)

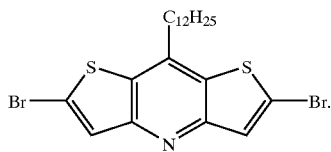

22. An oligo or a polymer made from at least one dithieno[3,2-b;2',3']pyridine and at least one reactive group.

23. An oligo, or a polymer according to claim 22, wherein the oligo or polymer is of the formula:

—[(Y)$_a$-(D)$_b$-(Z)$_c$]—  I wherein

D is a dithienopyridine group of formula II

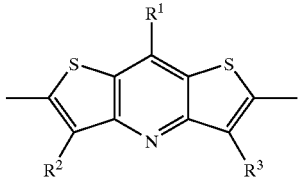

II $R^1$–$R^3$ are, independently of each other, H, halogen or straight chain, branched or cyclic alkyl with 1–20 C-atoms, which may be unsubstituted, mono- or poly-substituted by F, Cl, Br, I or CN, optionally one or more non-adjacent CH$_2$ groups are replaced, in each case independently from one another, by —O—, —S—, —NH—, —NR$^o$—, —SiR$^o$R$^{oo}$—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, $R^o$ and $R^{oo}$ are, independently of each other, H or alkyl with 1–12 C-atoms, Y and Z are, independently of each other, —CX$^1$=CX$^2$—, —C≡C—, or optionally substituted arylene or heteroarylene, $X^1$ and $X^2$ are, independently of each other, H, F, Cl or CN, and a, b and c are, independently of each other, 0 or 1, with a+b+c>0, and wherein at least one recurring unit b is 1.

24. An oligo- or a polymer according to claim 23, wherein if b=1 and a=c=o, at least one of $R^2$ and $R^3$ is different from H.

25. A side chain liquid crystal polymer made by polymerizing one or more monomers, oligomers, or polymers comprising at least one dithienopyridine group optionally with one or more additional mesogenic or nonmesogenic comonomers.

26. A side chain liquid polymer made by grafting one or more monomers, oligomers, or polymers comprising at least one dithienopyridine group to a polymer backbone in a polymer analogous reaction, optionally with one or more additional mesogenic or nonmesogenic comonomers.

27. An oligomer or a polymer comprising at least one dithienopyridine group.

28. A mono-, an oligo- or a polymer, of formula I1

R$^4$—[(Y)$_a$-(D)$_b$-(Z)$_c$]$_n$-R$^5$  I1 wherein

D is a dithienopyridine group of formula II

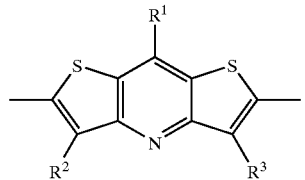

II $R^1$–$R^3$ are, independently of each other, H, halogen or straight chain, branched or cyclic alkyl with 1–20 C-atoms, which may be unsubstituted, mono- or poly-substituted by F, Cl, Br, I or CN, optionally one or more non-adjacent CH$_2$ groups are replaced, in each case independently from one another, by —O—, —S—, —NH—, —NR$^o$—, —SiR$^o$R$^{oo}$—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, $R^o$ and $R^{oo}$ are, independently of each other, H or alkyl with 1–12 C-atoms, Y and Z are, independently of each other, —CX$^1$=CX$^2$—, —C≡C—, or optionally substituted arylene or heteroarylene, $X^1$ and $X^2$ are, independently of each other, H, F, Cl or CN, $R^4$ and $R^5$ are, independently of each other, H, halogen, Sn(R$^o$)$_3$ or straight chain, branched or cyclic alkyl with 1–20 C-atoms, which may be unsubstituted, mono- or poly-substituted by F, Cl, Br, I or CN, optionally one or more non-adjacent CH$_2$ groups are replaced, in each case independently from one another, by —O—, —S—, —NH—, —NR$^o$—, —SiR$^o$R$^{oo}$—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, or denote P-Sp-X, a, b and c are, independently of each other, 0 or 1, with a+b+c>0, and wherein at least one recurring unit b is 1, and if b=1 and a=c=o, at least one of $R^4$ and $R^5$ is different from H, n is an integer 1–5000, P is a polymerisable or reactive group, Sp is a spacer group or a single bond, and X is —O—, —S—, —OCH$_2$—, —CH$_2$O—, —CO—, —COO—, —OCO—, —OCO—O—, —CO—NR$^o$—, —NR$^o$—CO—, —OCH$_2$—, —CH$_2$O—, —SCH$_2$—, —CH$_2$S—, —CH=CH—COO—, —OOC—CH=CH— or a single bond, and wherein the recurring units [(Y)$_a$-(D)$_b$-(Z)$_c$] can be identical or different.

* * * * *

UNITED STATES PATENT AND TRADEMARK OFFICE
CERTIFICATE OF CORRECTION

PATENT NO. : 6,841,677 B2
DATED : January 11, 2005
INVENTOR(S) : Martin Heeney et al.

It is certified that error appears in the above-identified patent and that said Letters Patent is hereby corrected as shown below:

Tilte page,
Item [54], Title, should read -- MONO-, OLIGO- AND POLYDITHIENOPYRIDINES --.

Column 23,
Line 50, "A" should read -- An --.
Line 55, "comprising" should read -- which comprises --.

Column 28,
Line 32, "is" should read -- are --.

Signed and Sealed this

Twenty-fourth Day of May, 2005

JON W. DUDAS
*Director of the United States Patent and Trademark Office*